US012521502B2

(12) United States Patent
Aoyagi et al.

(10) Patent No.: US 12,521,502 B2
(45) Date of Patent: Jan. 13, 2026

(54) NASAL ADAPTOR AND RESPIRATORY MANAGEMENT DEVICE

(71) Applicant: NIHON KOHDEN CORPORATION, Tokyo (JP)

(72) Inventors: Takayuki Aoyagi, Tokorozawa (JP); Kenichiro Kabumoto, Tokorozawa (JP); Fumihiko Takatori, Tokorozawa (JP); Masayuki Inoue, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 1253 days.

(21) Appl. No.: 17/281,384

(22) PCT Filed: Nov. 14, 2019

(86) PCT No.: PCT/JP2019/044747

§ 371 (c)(1),
(2) Date: Mar. 30, 2021

(87) PCT Pub. No.: WO2020/121732

PCT Pub. Date: Jun. 18, 2020

(65) Prior Publication Data

US 2022/0031981 A1 Feb. 3, 2022

(30) Foreign Application Priority Data

Dec. 10, 2018 (JP) ................................ 2018-231161

(51) Int. Cl.
*A61M 16/00* (2006.01)
*A61M 16/06* (2006.01)

(52) U.S. Cl.
CPC .... *A61M 16/0003* (2014.02); *A61M 16/0666* (2013.01); *A61M 2230/432* (2013.01)

(58) Field of Classification Search
CPC .......... A61M 16/0003; A61M 16/0666; A61M 2230/432; A61M 16/0009;
(Continued)

(56) References Cited

U.S. PATENT DOCUMENTS 5,046,491 A * 9/1991 Derrick ............. A61M 16/0611 128/911
9,833,586 B2 * 12/2017 Yokota ............. A61M 16/0488
(Continued)

FOREIGN PATENT DOCUMENTS

| | | | |
|---|---|---|---|
| EP | 2 702 942 | A1 | 3/2014 |
| JP | 2009-066431 | A | 4/2009 |
| JP | 2013-180182 | A | 9/2013 |

OTHER PUBLICATIONS

Japanese Office Action dated Aug. 16, 2022 issued in Japanese Patent Application No. 2018-231161 .
(Continued)

*Primary Examiner* — Victoria Murphy
*Assistant Examiner* — Tina Zhang
(74) *Attorney, Agent, or Firm* — McDonald Hopkins LLC

(57) ABSTRACT

A nasal adaptor includes: an oral expiration guiding portion which has an opposing portion that is to be opposed to the mouth of a living body, and in which a mouth-side guide path that guides expiration that is expired from the mouth to the opposing portion is formed; and an attaching portion which is placed above the oral expiration guiding portion with respect to the living body, and to which a holding member that holds a sensor for measuring the expiration guided by the oral expiration guiding portion is attached. The oral expiration guiding portion is integrally connected to the attaching portion, and has positioning changing portions that change the distances between connecting portions connected to the attaching portion, and the opposing portion, thereby changing the positioning of the opposing portion.

12 Claims, 7 Drawing Sheets

(58) Field of Classification Search
CPC ...... A61M 2016/0042; A61M 16/0672; A61M 16/085; A61M 16/0858; A61M 16/0605; A61M 16/0644; A61M 16/065; A61M 16/0655; A61M 2230/43; A61M 16/0683; A61M 16/06; A61M 2210/0625; A61M 2202/0208; A61M 16/0816; A61B 5/0836; A61B 5/097; A61B 5/0873; A61B 5/082; A63B 2230/40; A62B 9/06; B63C 11/186; B63C 11/205
USPC ..... D24/110.5; 600/532, 543, 529, 538, 301
See application file for complete search history.

(56) References Cited

U.S. PATENT DOCUMENTS

2004/0182396 A1 9/2004 Dennis
2004/0206907 A1 10/2004 Yamamori et al.
2005/0022820 A1* 2/2005 Kwok ............... A61M 16/0616 128/206.24
2006/0247551 A1 11/2006 Yamamori et al.
2010/0317987 A1* 12/2010 Inoue .................. A61M 16/125 600/543
2011/0094513 A1* 4/2011 Takatori ............ A61M 16/0875 128/202.16
2013/0231540 A1 9/2013 Inoue et al.
2015/0099986 A1* 4/2015 Inoue ..................... A62B 9/006 600/479
2016/0184544 A1 6/2016 Patel et al.
2017/0007795 A1* 1/2017 Pedro ..................... A61B 5/082

OTHER PUBLICATIONS

International Search Report dated Feb. 13, 2020 issued in Patent Application No. PCT/JP2019/044747.
Written Opinion dated Feb. 13, 2020 issued in Patent Application No. PCT/JP2019/044747.

* cited by examiner

NASAL ADAPTOR AND RESPIRATORY MANAGEMENT DEVICE

TECHNICAL FIELD

The presently disclosed subject matter relates to a nasal adaptor and a respiratory management device, and more particularly to a nasal adaptor and respiratory management device that are used for measuring expiration expired from the mouth of a living body.

BACKGROUND ART

Conventionally, a nasal adaptor for measuring expiration expired from the mouth and nose of a living body has been practically used. A nasal adaptor is to be attached to the face of a living body, and, for example, has: an attaching portion to which a sensor for measuring the concentration of carbon dioxide contained in expiration is to be attached; and an oral expiration guiding portion that is placed below the attaching portion so as to be opposed to the mouth. The oral expiration guiding portion is formed so as to guide respiration expired from the mouth, toward the sensor.

The concentration of carbon dioxide contained in the expiration can be sequentially measured by the sensor.

However, the oral expiration guiding portion is to be placed in proximity to the mouth, and therefore there is a risk that the portion is in contact with the mouth and its periphery, and the subject feels a sense of discomfort.

As a technique for suppressing contact of an oral expiration guiding portion with a living body, for example, Patent Literature 1 therefore proposes an airway adaptor in which, in the case where a plurality of kinds of physiological information are to be acquired, the work of attaching the adaptor to the subject can be efficiently performed, and botheration that is felt by the subject can be suppressed. In the airway adaptor, the oral expiration guiding portion is swingably connected through a support shaft to an attaching portion, and therefore the positioning of the oral expiration guiding portion can be changed to suppress contact of the portion with the living body.

CITATION LIST

Patent Literature

[PTL 1] JP-A-2013-180182

SUMMARY OF INVENTION

Technical Problem

When the oral expiration guiding portion is connected to the attaching portion through the support shaft, however, the attaching portion and the oral expiration guiding portion must be separately produced, and therefore there is a problem in that the number of components is increased.

The presently disclosed subject matter has been conducted in order to solve the problem of the prior art. It is an object of the presently disclosed subject matter to provide a nasal adaptor and respiratory management device in which the positioning of an oral expiration guiding portion can be changed by a simple configuration.

Solution to Problem

The nasal adaptor of the presently disclosed subject matter includes:

an oral expiration guiding portion which has an opposing portion that is to be opposed to a mouth of a living body, and in which a mouth-side guide path that guides expiration that is expired from the mouth to the opposing portion is formed; and an attaching portion which is placed above the oral expiration guiding portion with respect to the living body, and to which a measurement member that holds a sensor for measuring the expiration guided by the oral expiration guiding portion, or a tubular measurement member that guides the expiration to an external device is attached, and the oral expiration guiding portion is integrally connected to the attaching portion, and has a positioning changing portion that changes a distance between a connecting portion connected to the attaching portion, and the opposing portion, thereby changing a positioning of the opposing portion.

The respiratory management device of the presently disclosed subject matter includes: the above-described nasal adaptor; and a nasal cannula that has a tubular shape, and that is attached to the nasal adaptor in order to supply a predetermined gas to at least one of the nostrils and the mouth.

Advantageous Effects of Invention

According to the presently disclosed subject matter, the oral expiration guiding portion is integrally connected to the attaching portion, and the positioning changing portion changes the distance between the connecting portion connected to the attaching portion, and the opposing portion, thereby changing the positioning of the opposing portion, and therefore it is possible to provide a nasal adaptor and respiratory management device in which the positioning of the oral expiration guiding portion can be changed by a simple configuration.

DESCRIPTION OF EMBODIMENTS

Hereinafter, embodiments of the presently disclosed subject matter will be described with reference to the accompanying drawings.

Embodiment 1

Figure 1:
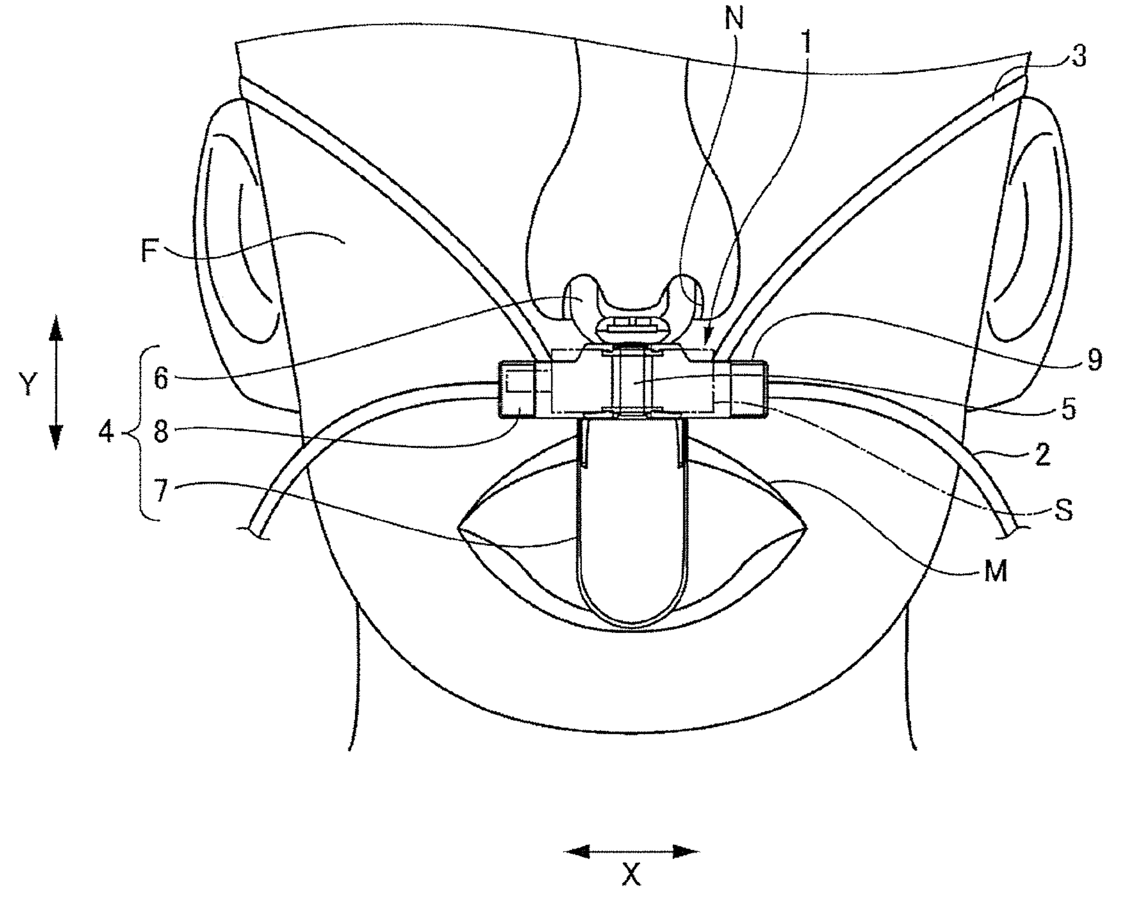
FIG. 1 illustrates the configuration of a respiratory management device of Embodiment 1 of the presently disclosed subject matter.

FIG. 1 illustrates the configuration of a respiratory management device including a nasal adaptor of Embodiment 1 of the presently disclosed subject matter. The respiratory management device is to be attached to the face F of a living body, and may include a nasal adaptor 1, a pair of nasal cannulas 2, and a fixing band portion 3.

The nasal adaptor 1 may include the adaptor body 4 that is to be placed in front of the face F, and a holding member 5 that is to be attached to the adaptor body 4.

The adaptor body 4 may include a nasal expiration guiding portion 6 that is placed in correspondence with the nostrils N of the living body, an oral expiration guiding portion 7 that is placed in correspondence with the mouth M of the living body, and an attaching portion 8 that is placed between the nasal expiration guiding portion 6 and the oral expiration guiding portion 7.

Here, the nasal expiration guiding portion 6, the oral expiration guiding portion 7, and the attaching portion 8 are integrally formed by a flexible material. Examples of the flexible material are a vinyl chloride resin, etc.

The nasal expiration guiding portion 6 guides expiration ejected from the nostrils N toward the holding member 5, and is formed to extend from the attaching portion 8 toward the two nostrils N with branching off.

The attaching portion 8 is placed to extend in the lateral direction X with respect to the living body, and formed so that the holding member 5 can be attached to cover the middle part of the attaching portion. The attaching portion 8 is further formed so that the nasal cannulas 2 can be attached to lateral side parts, respectively, and the fixing band portion 3 can be attached to the vicinities of the lateral side parts.

The oral expiration guiding portion 7 guides expiration ejected from the mouth M, toward the holding member 5, and is formed to extend in front of the mouth M and in the vertical direction Y.

The holding member 5 holds a sensor S that measures expiration which is guided by the nasal expiration guiding portion 6 and the oral expiration guiding portion 7, and is formed so that the sensor S is attachable to and detachable from the holding member. The holding member 5 is formed to have a rigidity that is higher than the rigidities of the nasal expiration guiding portion 6, the oral expiration guiding portion 7, and the attaching portion 8. Here, the holding member 5 is placed on the side of the attaching portion 8 that is opposite to the face F of the living body, and attached to the attaching portion 8 to cover a part of the attaching portion 8 in order to support the attaching portion 8. For example, the holding member 5 may be configured by a thermoplastic resin. The holding member 5 constitutes the measurement member in the presently disclosed subject matter.

As the sensor S, for example, a sensor that measures the concentration of carbon dioxide contained in expiration may be used.

The pair of nasal cannulas 2 have a tubular shape. In order to supply a predetermined gas to the nostrils N, one end parts of the pair of nasal cannulas 2 are attached to the lateral end parts of the attaching portion 8, respectively. The nasal cannulas 2 are formed to extend to a gas supply device that is not illustrated, and that supplies the predetermined gas, and their other end parts are connected to the gas supply device. For example, a device that supplies oxygen may be used as the gas supply device. Here, gas supplying portions 9*a* and 9*b* that open toward the nostrils N and the mouth M are formed in an upper part of the attaching portion 8, respectively. Oxygen that is guided to the attaching portion 8 by the nasal cannulas 2 is discharged to the peripheries of the nostrils N through the gas supplying portion 9*a*, and also to the periphery of the mouth M through the gas supplying portion 9*b*.

The fixing band portion 3 is used for fixing the nasal adaptor 1 to the face F of the living body, and extends to surround the periphery of the face F, and the both end parts of the fixing band portion are attached to the attaching portion 8.

Next, the configuration of the nasal adaptor 1 will be described in detail.

Figure 2A:
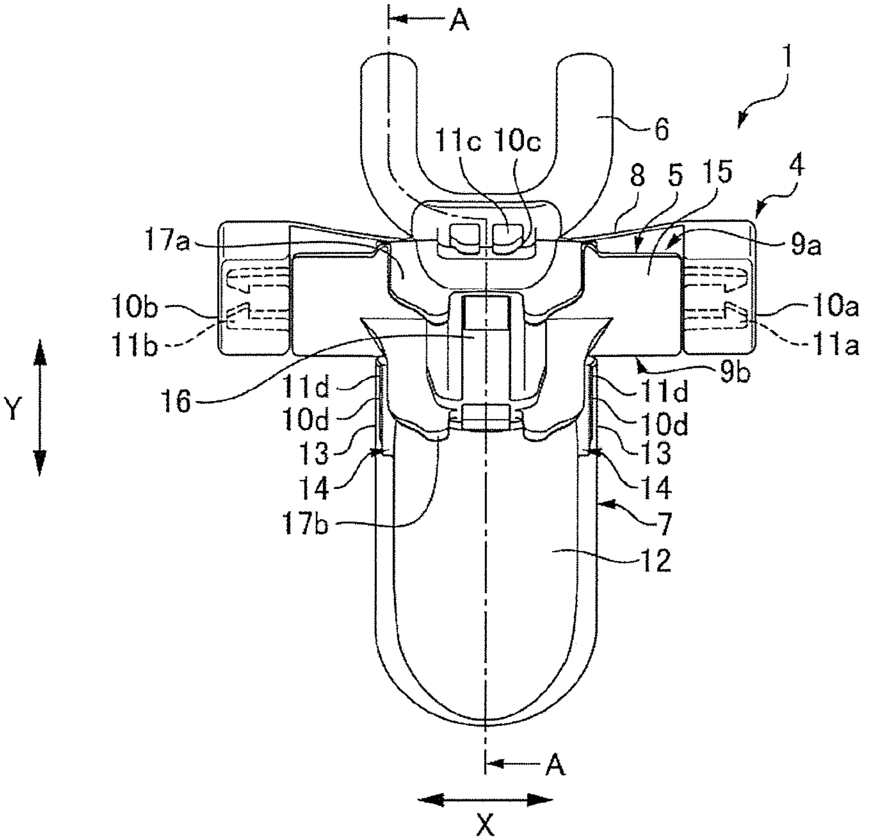
FIGS. 2A and 2B illustrate the configuration of a nasal adaptor.
Figure 2B:
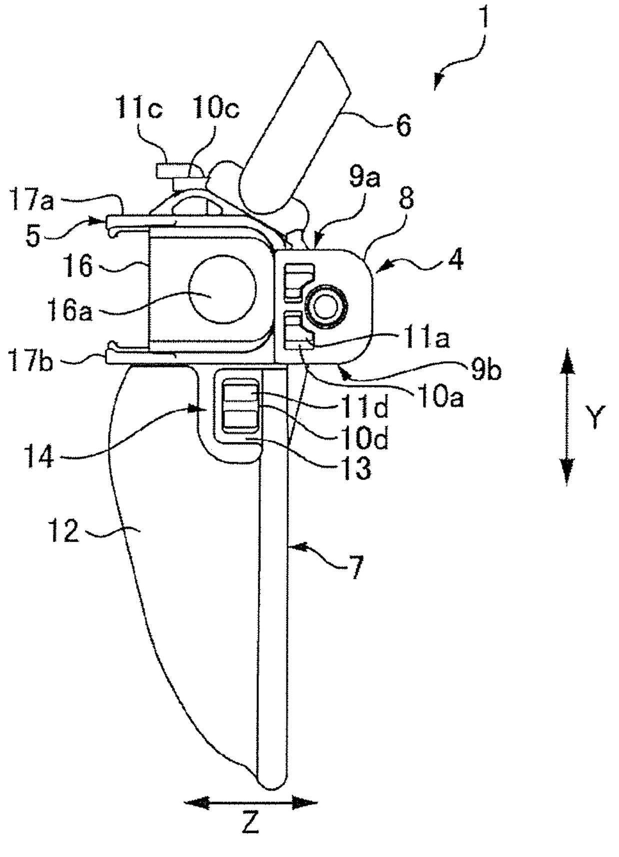

As illustrated in FIGS. 2A and 2B, the nasal expiration guiding portion 6 is integrally connected to an upper part of the attaching portion 8, and the oral expiration guiding portion 7 is integrally connected to a lower part of the attaching portion 8. The attaching portion 8 is formed to extend in the rear of the holding member 5, i.e., in the lateral direction X and on the side of the face F with respect to the holding member 5. By contrast, the holding member 5 may include a back plate portion 15 that is formed to extend in the lateral direction X and in front of the attaching portion 8 while forming a gap with the attaching portion 8. Therefore, the supplying portions 9*a* and 9*b* that open toward the nostrils N and the mouth M, respectively are formed between the attaching portion 8 and the back plate portion 15.

An attachment hole 10*a* is disposed in a right part of the attaching portion 8, and an attachment hole 10*b* is disposed in a left part of the attaching portion 8. In the back plate portion 15 of the holding member 5, a right fixing part 11*a* is disposed so as to be insertable into the attachment hole 10*a*, and a left fixing part 11*b* is disposed so as to be insertable into the attachment hole 10*b*. When the right fixing part 11*a* is inserted into the attachment hole 10*a*, the right part of the attaching portion 8 is fixed to the holding member 5 so as to stretch in the rightward direction, and, when the left fixing part 11*b* is inserted into the attachment hole 10*b*, the left part of the attaching portion 8 is fixed to the holding member 5 so as to stretch in the leftward direction.

Attachment holes 10*c* are disposed in an upper part of the attaching portion 8, and attachment holes 10*d* are disposed in a lower part of the attaching portion 8. In the holding member 5, upper fixing parts 11*c* are disposed in correspondence with the attachment holes 10*c*, and lower fixing parts 11*d* are disposed in correspondence with the attachment holes 10*d*, respectively. When the upper fixing parts 11*c* are inserted into the attachment holes 10*c*, the upper part of the attaching portion 8 is fixed to the holding member 5 so as to stretch in the upward direction, and, when the lower fixing parts 11*d* are inserted into the attachment holes 10*d*, the lower part of the attaching portion 8 is fixed to the holding member 5 so as to stretch in the downward direction.

The oral expiration guiding portion 7 may include an opposing portion 12, connecting portions 13, and positioning changing portions 14.

The opposing portion 12 is formed into a cup-like shape that extends immediately below the holding member 5, and that is arcuated toward the front side, and placed to be opposed to the mouth M of the living body.

The connecting portions 13 are placed in a pair of side parts of the oral expiration guiding portion 7, respectively, and integrally connected to the attaching portion 8. That is, the oral expiration guiding portion 7 is connected to the attaching portion 8, only through the pair of side parts, and the part between the side parts is not connected to but separated from the attaching portion 8.

The positioning changing portions 14 are formed by cutting out the vicinities of the connecting portions 13 so that the distances between the connecting portions 13 and the opposing portion 12 are changed, peripherally about a straight line that connects the pair of side parts of the oral expiration guiding portion 7 with each other. Specifically, the positioning changing portions 14 are formed by cutting out the gaps between the connecting portions 13 and the opposing portion 12 in an L-like shape or in the vertical direction Y and the anteroposterior direction Z. In other words, each of the positioning changing portions 14 has a cut out shape that opens and closes the gap between the corresponding connecting portion 13 and the opposing portion 12. Therefore, the positioning changing portions 14 change the positioning of the opposing portion 12 so as to change the distance with respect to the connecting portions 13, while using the straight line that connects the pair of side parts of the oral expiration guiding portion 7 with each other, as a virtual swing axis.

Figure 3:
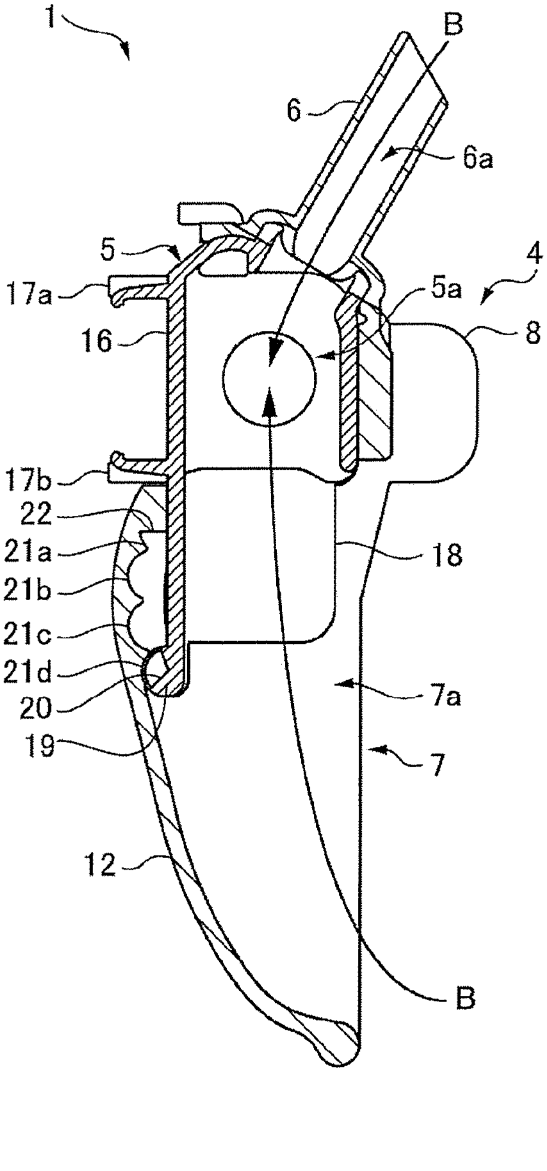
FIG. 3 is a sectional view taken along line A-A in FIG. 2A.

As illustrated in FIG. 3, a nose-side guide path 6*a* that guides expiration B that is expired from the nostrils N, toward the holding member 5 is formed in the nasal expiration guiding portion 6.

Moreover, a mouth-side guide path 7*a* that guides expiration B that is expired from the mouth M to the opposing portion 12, toward the holding member 5 is formed in the oral expiration guiding portion 7. Furthermore, a communication path 5*a* that communicates with the nose-side guide path 6*a* and the mouth-side guide path 7*a* is formed in the holding member 5. According to the configuration, the expiration B expired from the nostrils N is guided to the communication path 5*a* through the nose-side guide path 6*a*, and the expiration B expired from the mouth M is guided to the communication path 5*a* through the mouth-side guide path 7*a*.

Figure 4:
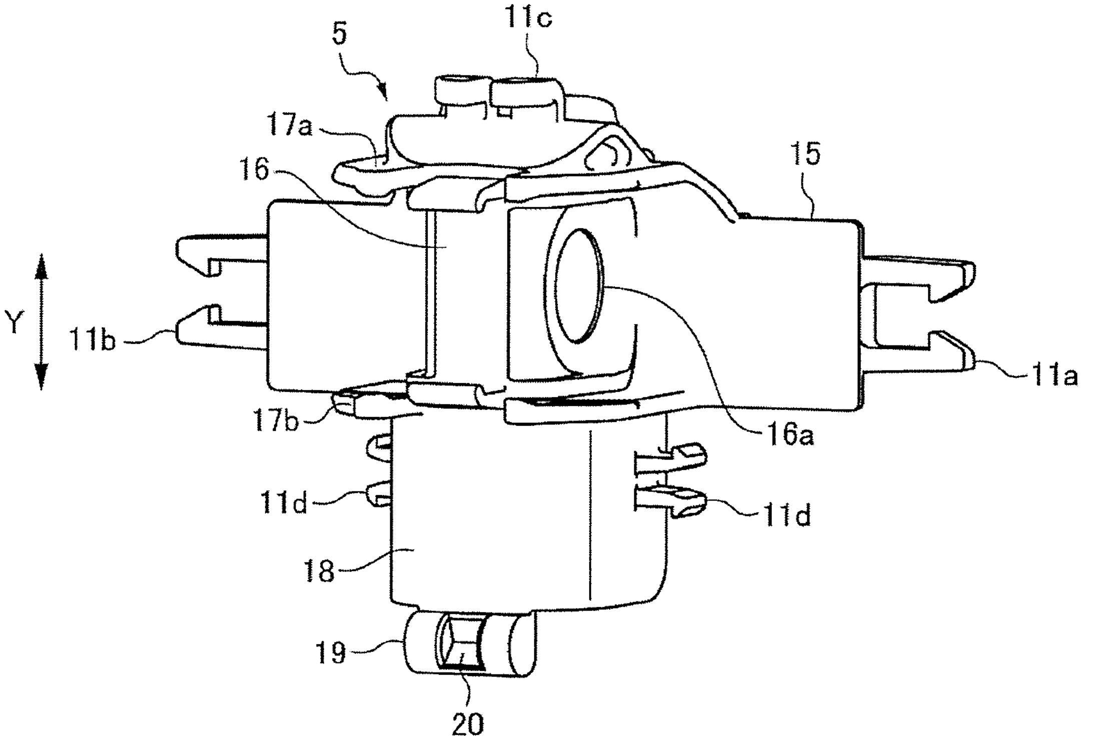
FIG. 4 is a perspective view illustrating the configuration of a holding member.

As illustrated in FIG. 4, the holding member 5 may include: a column part 16 that forwardly projects in a column-like manner from a middle part of the back plate portion 15; a pair of projecting parts 17*a* and 17*b* that forwardly project from upper and lower parts of the back plate portion 15 so as to clamp the column part 16, respectively; a supporting portion 18 that is formed so as to downward protrude from the projecting part 17*b*; and a protruding part 19 that forwardly protrudes from a lower part of the supporting portion 18.

The sensor S that is not illustrated in the figure is attached to the both side parts of the column part 16 so as to clamp the column part. Windows 16*a* for measuring the expiration B flowing through the communication path 5*a* that is formed in the column part 16 are formed in the both side parts, respectively. For example, the sensor S outputs an infrared light beam or the like toward the windows 16*a*, and measures the concentration of carbon dioxide contained in the expiration B based on the change of the amount of the infrared light beam that passes through the windows 16*a*.

The pair of projecting parts 17*a* and 17*b* support the sensor S that is not illustrated in the figure, in the vertical direction Y, and are placed so as to clamp the sensor S in the vertical direction Y.

The supporting portion 18 supports the positioning of the opposing portion 12, extends into the mouth-side guide path 7*a* of the oral expiration guiding portion 7, and is placed so as to be opposed to the rear surface of the opposing portion 12. The supporting portion 18 is formed to be forwardly curved into a U-like shape and along the rear surface of the opposing portion 12. The lower fixing parts 11*d* are disposed on the both side parts of the supporting portion, respectively.

The protruding part 19 is placed in a middle part of the supporting portion 18 in the lateral direction X, and formed to protrude from the supporting portion 18 toward the rear surface of the opposing portion 12. In a middle part of the protruding part 19, moreover, a concave part 20 is formed so that an upper part is downwardly recessed.

Figure 5:
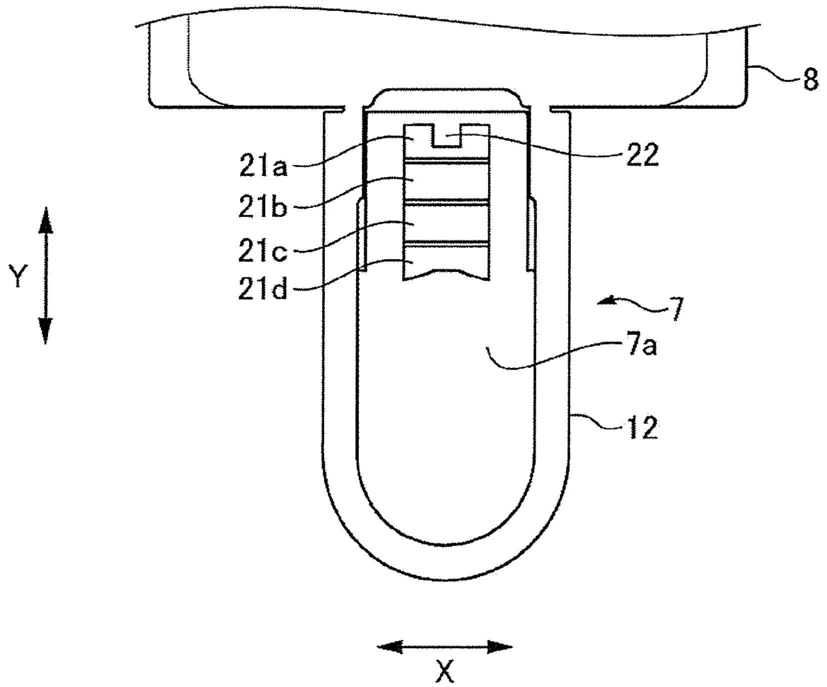
FIG. 5 illustrates the configuration of the rear surface of an opposing portion.

As illustrated in FIG. 5, four receiving parts 21*a*, 21*b*, 21*c*, and 21*d* that are recessed in correspondence to the protruding part 19 of the holding member 5 are formed in the rear surface of the opposing portion 12. When the protruding part 19 is engaged with one of the receiving parts 21*a* to 21*d*, the positioning of the opposing portion 12 is supported with respect to the supporting portion 18. The receiving parts 21*a* to 21*d* are arranged in the vertical direction Y. When the protruding part 19 is engaged with a different one of the receiving parts 21*a* to 21*d*, the positioning of the opposing portion 12 can be stepwise changed. A convex part 22 that protrudes so as to be engaged with the concave part 20 of the protruding part 19 is formed in the receiving part 21*a* that is located in the highest position among the receiving parts 21*a* to 21*d*.

Next, the operation of the embodiment will be described.

As illustrated in FIG. 1, first, the nasal adaptor 1 is fixed to the face F of the living body by the fixing band portion 3. At this time, the nasal adaptor 1 is fixed so that the nasal expiration guiding portion 6 is inserted into the nostrils N, and the oral expiration guiding portion 7 is opposed to the mouth M.

Here, the holding member 5 is placed so as to cover a part of the attaching portion 8. Therefore, the holding member 5 supports the attaching portion 8, and also the nasal expiration guiding portion 6 and oral expiration guiding portion 7 that are arranged so as to clamp the attaching portion 8 in the vertical direction Y, and hence the positioning of the nasal expiration guiding portion 6, oral expiration guiding portion 7, and attaching portion 8 that are formed by a flexible material can be maintained. Consequently, the nasal expiration guiding portion 6, the oral expiration guiding portion 7, and the attaching portion 8 can be integrally formed by a flexible material, the number of the components can be reduced, and the nasal adaptor 1 can be formed by a simple configuration. Moreover, the nasal expiration guiding portion 6 and the oral expiration guiding portion 7 can be prevented from dropping off from the attaching portion 8. Furthermore, the formation of the oral expiration guiding portion 7 by a flexible material can prevent the skin of the living body from, when the oral expiration guiding portion 7 is in contact with the living body, being damaged.

The holding member 5 has a rigidity that is higher than the rigidities of the nasal expiration guiding portion 6, the oral expiration guiding portion 7, and the attaching portion 8, and therefore can strongly support the nasal expiration guiding portion 6, the oral expiration guiding portion 7, and the attaching portion 8.

Moreover, the holding member 5 fixes the upper and lower parts of the attaching portion 8 so that the attaching portion 8 stretches in the vertical direction Y, and the right and left parts of the attaching portion 8 so that the attaching portion 8 stretches in the lateral direction X. Therefore, the nasal expiration guiding portion 6, the oral expiration guiding portion 7, and the attaching portion 8 can be supported more strongly.

In this way, the positioning of the nasal expiration guiding portion 6 that is inserted into the nostrils N is maintained, and that of the oral expiration guiding portion 7 that is placed in opposition to the mouth M is maintained. As illustrated in FIG. 3, then, the expiration B expired from the nostrils N is guided to the nose-side guide path 6*a* of the nasal expiration guiding portion 6, and flows into the communication path 5*a* of the holding member 5, and the expiration B expired from the mouth M is guided to the mouth-side guide path 7*a*, and flows into the communication path 5*a* of the holding member 5. Then, the concentration of carbon dioxide contained in the expiration that flows in the communication path 5*a* is measured by the sensor S.

At this time, the positioning of the nasal expiration guiding portion 6 and the oral expiration guiding portion 7 are maintained. Therefore, the expiration B expired from the nostrils N and the mouth M can be stably guided to the communication path 5*a*, and the concentration of carbon dioxide contained in the expiration B can be accurately measured.

Figure 6:
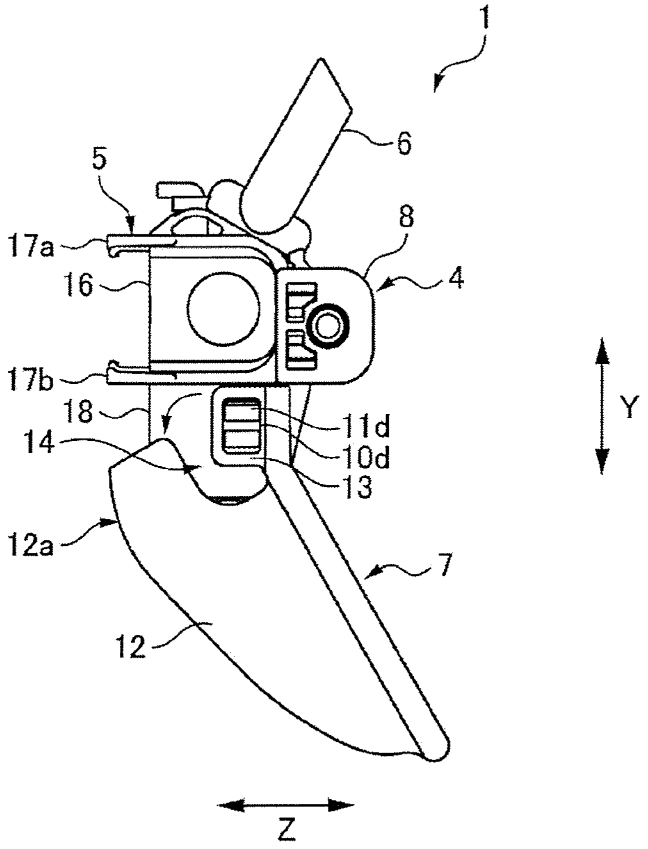
FIG. 6 is a side view illustrating a manner of changing the positioning of the opposing portion.

In the case where the subject wishes to make the opposing portion 12 of the oral expiration guiding portion 7 approach to the mouth M, as illustrated in FIG. 6, the positioning of the opposing portion 12 is changed so that the opposing portion swings about the straight line that connects the pair of side parts of the oral expiration guiding portion 7 with each other. At this time, the positioning changing portions 14 change the positioning of the opposing portion 12 so that the distance between the connecting portions 13 and the opposing portion 12 is increased about the straight line that connects the pair of side parts of the oral expiration guiding portion 7 with each other, i.e., the positioning changing portions 14 largely open. In each of the positioning changing portions 14, specifically, the positioning of the opposing portion 12 is changed by separating, from the connecting portions 13, a distance changing part 12*a* that is in the front side of the opposing portion 12, the connecting portions 13 and the distance changing part 12*a* being located across the positioning changing portion 14 in the anteroposterior direction Z.

According to the configuration, in the state where the oral expiration guiding portion 7 is integrally connected to the attaching portion 8, the positioning of the opposing portion 12 can be easily changed so that the opposing portion 12 approaches the mouth M. Namely, the positioning of the opposing portion 12 can be changed simply by causing the positioning changing portion 14 to open, without bending the connecting portions 13 by a large force.

As described above, the positioning of the opposing portion 12 that is integrally connected to the attaching portion 8 can be easily changed by the simple configuration. Moreover, the positioning changing portions 14 are formed so that the gaps between the respective connecting portions 13 and the opposing portion 12 are cut out in an L-like shape. Therefore, the cut-out gaps can largely open not only in the anteroposterior direction Z but also in the vertical direction Y, and the positioning of the opposing portion 12 can largely be changed.

When the distance between the mouth M and the opposing portion 12 is changed as described above, it is possible to prevent a situation where the opposing portion 12 is in contact with the mouth M and its periphery, and the subject feels a sense of discomfort, from occurring. When the positioning of the opposing portion 12 is changed in accordance with the shape of the mouth M, moreover, it is possible to prevent the expiration B expired from the mouth M, from flowing out to the outside of the opposing portion 12. In the case of a subject in whom the upper lip is protrude more than the lower lip, when the positioning of the opposing portion 12 remains unchanged, for example, the lower part of the opposing portion 12 separates from the lower lip, and therefore there arises a risk that the expiration B expired from the mouth M flows out through the lower side of the opposing portion 12. Therefore, the positioning of the opposing portion 12 is changed so that the lower portion of the opposing portion 12 approaches the lower lip, whereby the expiration B expired from the mouth M is caused to surely flow in the interior of the opposing portion 12.

As illustrated in FIG. 4, moreover, the protruding part 19 is disposed on the supporting portion 18 of the holding member 5. As illustrated in FIG. 5, furthermore, the four receiving parts 21*a* to 21*d* are formed on the rear surface of the opposing portion 12. In the case where the positioning of the opposing portion 12 is not changed, the protruding part 19 is engaged with the receiving part 21*d*. In the case where the opposing portion 12 has an inclined positioning as illustrated in FIG. 6, by contrast, the protruding part 19 is engaged with another one of the receiving parts 21*a* to 21*d*, i.e., for example, the receiving part 21*b*. As a result, the positioning of the opposing portion 12 is supported by the supporting portion 18, and therefore the positioning of the opposing portion 12 can be stepwise changed in accordance with various shapes of the mouth M.

Figure 7:
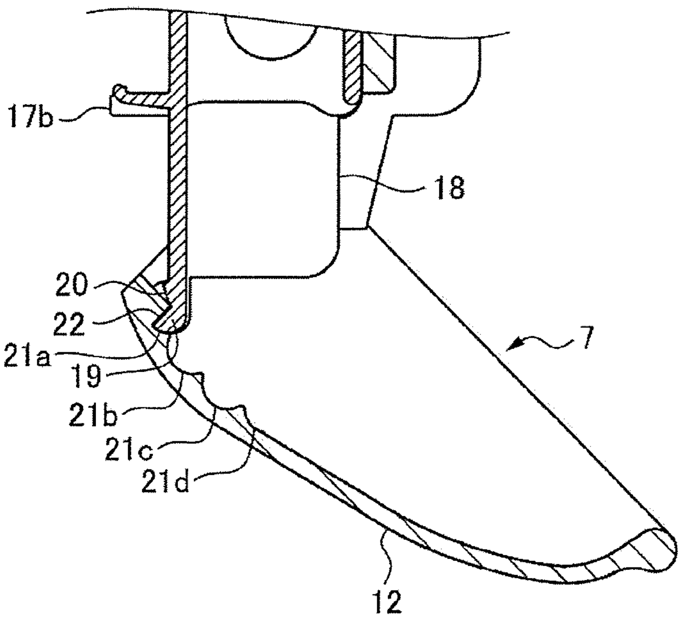
FIG. 7 is a sectional view illustrating a manner of engaging a convex part that is formed in a receiving portion, with a concave part of a protruding part.

When the positioning of the opposing portion 12 is inclined more largely, there arises a risk that the protruding part 19 of the holding member 5 moves to a position that is higher than the receiving part 21*a*, and the engagement is cancelled. As illustrated in FIG. 7, therefore, the convex part 22 is formed in the receiving part 21*a* that is located in the highest position among the receiving parts 21*a* to 21*d*, and, when the convex part 22 is engaged with the concave part 20 of the protruding part 19, the protruding part 19 can be prevented from moving to a position that is higher than the receiving part 21*a*. Therefore, it is possible to prevent the positioning of the opposing portion 12 from being largely changed without limitation, and the opposing portion 12 can be prevented from being disengaged from the supporting portion 18.

When the positioning of the opposing portion 12 is then restored so that the protruding part 19 is engaged with the receiving part 21*d*, the upper edge part of the opposing portion 12 butts against the supporting portion 18 of the holding member 5. Therefore, it is possible to prevent the positioning of the opposing portion 12 from being largely changed in the direction away from the mouth M. While maintaining a desired shape of the opposing portion 12, consequently, the concentration of carbon dioxide contained in the expiration expired from the nostrils N and the mouth M can be sequentially measured.

According to the embodiment, the positioning changing portions 14 are formed by cutting out the vicinities of the connecting portions 13 so that the distances between the connecting portions 13 and the opposing portion 12 are changed, and therefore the positioning of the opposing portion 12 can be changed by the simple configuration.

Embodiment 2

In Embodiment 1 above, the positioning changing portions 14 are formed by cutting out the vicinities of the connecting portions 13 so that the distances between the connecting portions 13 and the opposing portion 12 are changed about the straight line that connects the pair of side parts of the oral expiration guiding portion 7 with each other. However, the positioning changing portion is required to change the distances between the connecting portions 13 and the opposing portion 12, thereby changing the positioning of the opposing portion 12, and not limited to a configuration that is formed by cutting out.

Figure 8:
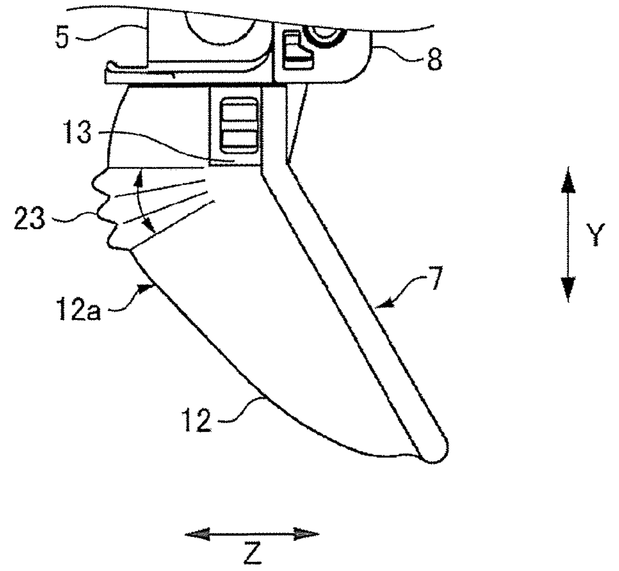
FIG. 8 is a side view illustrating the configuration of an oral expiration guiding portion in Embodiment 2.

As illustrated in FIG. 8, for example, a positioning changing portion 23 can be placed in place of the positioning changing portions 14 in Embodiment 1. The positioning changing portion 23 may include a bellows shape that causes the gaps between the connecting portions 13 and the opposing portion 12 to extend and contract about the straight line that connects the pair of side parts of the oral expiration guiding portion 7 with each other.

According to the configuration, in the case where the subject wishes to make the opposing portion 12 of the oral expiration guiding portion 7 approach the mouth M, the positioning of the opposing portion 12 is changed so as to incline toward the mouth M. At this time, the positioning of the opposing portion 12 is changed so that the distances between the connecting portions 13 and the opposing portion 12 are made large about the straight line that connects the pair of side parts of the oral expiration guiding portion 7 with each other, i.e., the positioning changing portion 23 extends. Specifically, the positioning changing portion 23 causes the distance changing part 12*a* that is in the front side of the opposing portion 12 to extend so as to separate from the connecting portions 13, thereby changing the positioning of the opposing portion 12, the connecting portions 13 and the distance changing part 12*a* being located across in the vertical direction Y. In the state where the oral expiration guiding portion 7 is integrally connected to the attaching portion 8, therefore, the positioning of the opposing portion 12 can be easily changed so that the opposing portion 12 approaches the mouth M.

According to the embodiment, the positioning changing portion 23 has the bellows structure that causes the gaps between the connecting portions 13 and the opposing portion 12 to extend and contract about the straight line that connects the pair of side parts of the oral expiration guiding portion 7 with each other, and therefore the positioning of the opposing portion 12 can be changed by the simple configuration.

In Embodiment 1 above, the positioning changing portions 23 in the embodiment may be added. In the nasal adaptor 1, namely, the positioning changing portion 23 in the embodiment and the positioning changing portions 14 in Embodiment 1 may be formed together. In the nasal adaptor 1, moreover, the positioning changing portion 23 in the embodiment, and the protruding part 19 and receiving parts 21*a* to 21*d* in Embodiment 1 may be formed together.

Embodiment 3

Although, in Embodiments 1 and 2 above, the supporting portion 18 is placed on the holding member 5, the supporting portion is required only to support the opposing portion 12, and not limited to be placed on the holding member 5.

Figure 9:
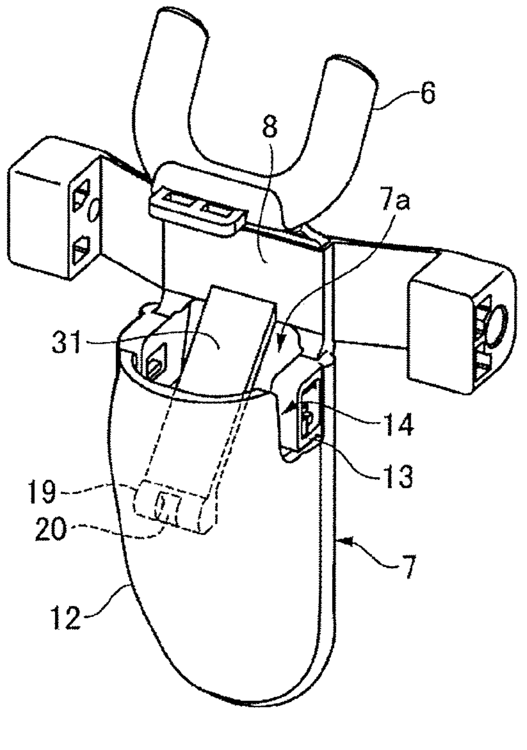
FIG. 9 is a perspective view illustrating the configuration of a supporting portion in Embodiment 3.

As illustrated in FIG. 9, for example, a supporting portion 31 may be placed in place of the supporting portion 18 in Embodiment 1. In FIG. 9, the illustration of the holding member 5 is omitted.

The supporting portion 31 has a planar shape that is integrally connected to the attaching portion 8, extends from the attaching portion 8 into the mouth-side guide path 7*a* of the oral expiration guiding portion 7, and is placed so as to be opposed to the rear surface of the opposing portion 12.

Namely, the supporting portion 31 is formed so as to extend from the attaching portion 8 toward the rear surface of the opposing portion 12 while being downward inclined. In the same or similar manner as Embodiment 1, moreover, the protruding part 19 is placed in the tip end of the supporting portion 31.

According to the configuration, in the case where the subject wishes to make the opposing portion 12 of the oral expiration guiding portion 7 approach the mouth M, the positioning of the opposing portion 12 is changed so as to swing about the straight line that connects the pair of side parts of the oral expiration guiding portion 7 with each other. Therefore, the protruding part 19 is engaged with one of the receiving parts 21*a* to 21*d* that are formed in the rear surface of the opposing portion 12, and the positioning of the opposing portion 12 can be stepwise changed.

According to the embodiment, the supporting portion 31 extends from the attaching portion 8 into the mouth-side guide path 7*a* of the oral expiration guiding portion 7, and is placed so as to be opposed to the rear surface of the opposing portion 12. Therefore, the supporting portion can support the positioning of the opposing portion 12.

Embodiment 4

Although, in Embodiments 1 to 3 above, the holding member 5 that holds the sensor S is attached to the attaching portion 8, the member which is to be attached to the attaching portion 8 is not limited to the holding member 5, and any member for measuring expiration that is guided the nasal expiration guiding portion 6 and the oral expiration guiding portion 7 may be attached.

Figure 10:
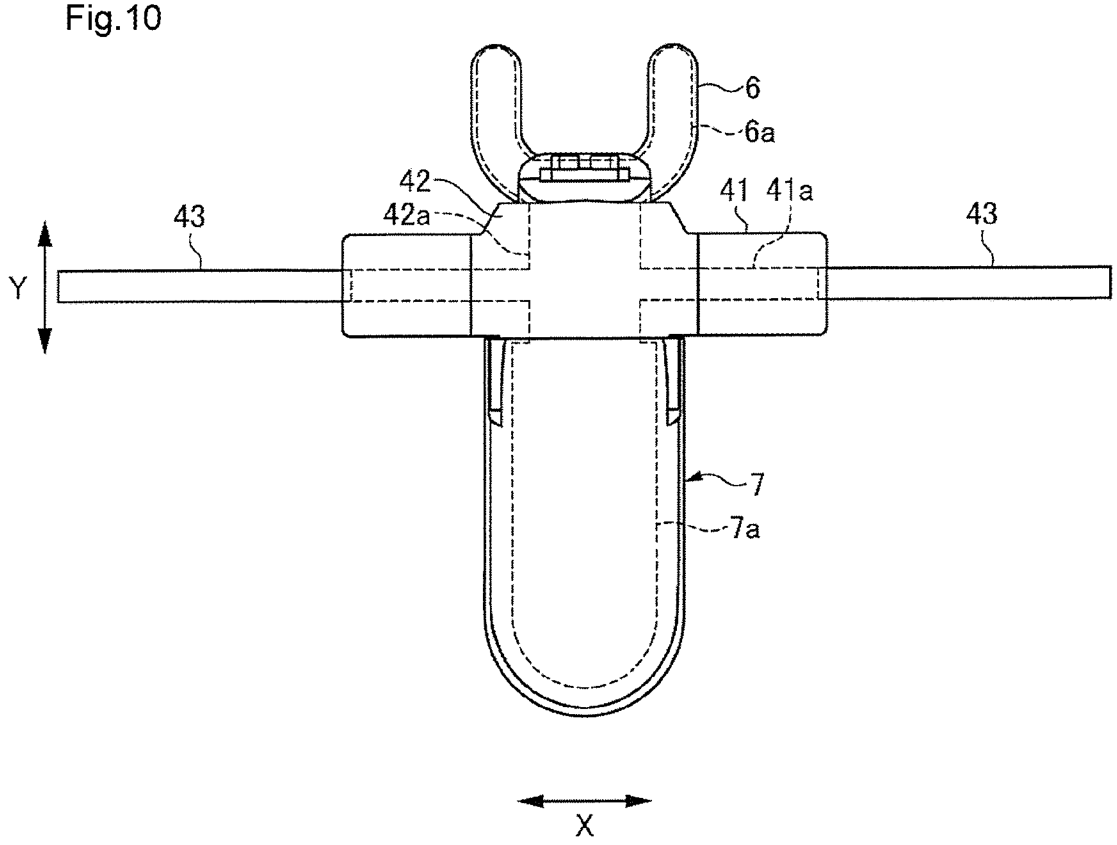
FIG. 10 is a front view illustrating the configuration of a nasal adaptor of Embodiment 4.

As illustrated in FIG. 10, for example, an attaching portion 41 may be placed in place of the attaching portion 8 in Embodiment 1, a guiding part 42 may be placed in place of the holding member 5, and a pair of measurement members 43 may be placed in place of the pair of nasal cannulas 2.

The attaching portion 41 is placed to extend in the lateral direction X, and formed so that the guiding part 42 can be attached to cover the middle part of the attaching portion. The attaching portion 41 is further formed so that the measurement members 43 can be attached to lateral side parts, respectively. Attachment-side guide paths 41*a* that are connected to the measurement members 43, respectively are formed in the attaching portion 41.

The guiding part 42 guides the expiration B that is guided by the nose-side guide path 6*a* of the nasal expiration guiding portion 6 and the mouth-side guide path 7*a* of the oral expiration guiding portion 7, toward the measurement members 43. In the guiding part 42, a communication path 42*a* that causes the nose-side guide path 6*a* and the mouth-side guide path 7*a* to communicate with the attachment-side guide paths 41*a* is formed. In the same or similar manner as the holding member 5 in Embodiment 1, the guiding part 42 is attached to the attaching portion 41 so as to cover the middle portion of the attaching portion 41.

The measurement members 43 guides the expiration B that flows from the attachment-side guide paths 41*a*, to an external device that is not illustrated, and has a tubular shape. One end parts of the measurement members 43 are attached to the lateral end parts of the attaching portion 41, and the other end parts are connected to the external device. As the external device, for example, a device for measuring the concentration of carbon dioxide contained in the expiration B may be used.

According to the configuration, the expiration B that is guided by the nose-side guide path 6*a* and the mouth-side guide path 7*a* flows through the interiors of the communication path 42*a*, the attachment-side guide paths 41*a*, and the measurement members 43 to reach the external device, and the concentration of carbon dioxide contained in the expiration B is sequentially measured by the external device.

According to the embodiment, the measurement members 43 that guides the expiration B to the external device is attached to the attaching portion 41, and therefore the concentration of carbon dioxide contained in the expiration B can be sequentially measured by the external device.

Although, in Embodiments 1 to 4 above, the nasal adaptor 1 is configured by the nasal expiration guiding portion 6, the attaching portion, the oral expiration guiding portion 7, and the measurement members, the configuration of the nasal adaptor is not limited to this as far as the oral expiration guiding portion 7 is integrally connected to the attaching portion. For example, the nasal adaptor 1 may be configured by the attaching portion and the oral expiration guiding portion 7.

Although, in Embodiments 1 to 4 above, the protruding part 19 is disposed on the supporting portion, and the receiving parts 21*a* to 21*d* that are recessed in correspondence to the protruding part 19 are formed in the rear surface of the opposing portion 12, the manner of supporting the positioning of the opposing portion 12 is not limited to this as far as the positioning of the opposing portion can be supported by causing the protruding part to be engaged with one of the receiving parts. For example, four protruding parts that protrude toward the supporting portion may be disposed on the rear surface of the opposing portion 12, and a receiving part that is recessed in correspondence to the protruding parts may be disposed in the supporting portion.

Although, in Embodiments 1 to 4 above, the four receiving parts 21*a* to 21*d* are disposed on the rear surface of the opposing portion 12, the number of the receiving parts is not limited to four as far as the protruding part 19 can be engaged with the receiving parts to cause the supporting portion to support the positioning of the opposing portion 12. For example, one receiving part may be disposed on the rear surface of the opposing portion 12.

The present application is based on Japanese Patent Application No. 2018-231161 filed on Dec. 10, 2018, the contents of which are incorporated herein by way of reference.

INDUSTRIAL APPLICABILITY

According to the invention, there is provided a nasal adaptor and respiratory management device in which the positioning of an oral expiration guiding device portion can be changed by a simple configuration.

The invention claimed is:

1. A nasal adaptor comprising:

an oral expiration guiding portion which includes an opposing portion that is to be opposed to a mouth of a living body, and in which a mouth-side guide path that guides expiration that is expired from the mouth to the opposing portion is formed; and an attaching portion being placed above the oral expiration guiding portion with respect to the living body, and to which a measurement member that holds a sensor for measuring the expiration guided by the oral expiration guiding portion is attached, or to which a tubular measurement member that guides the expiration to an external device is attached, wherein the oral expiration guiding portion is integrally connected to the attaching portion, and wherein the oral expiration guiding portion includes a positioning changing portion that changes an absolute distance between a connecting portion connected to the attaching portion, and a point on the opposing portion, thereby changing a positioning of the opposing portion.

2. The nasal adaptor according to claim 1, wherein the connecting portion is placed in a pair of side parts of the oral expiration guiding portion, and wherein the positioning changing portion comprises a cutout in a vicinity of the connecting portion so that the absolute distance between the connecting portion and the point on the opposing portion is configured to change about a straight line that connects the pair of side parts with each other.

3. The nasal adaptor according to claim 1, wherein the positioning changing portion is configured to have a bellows shape that causes a gap between the connecting portion and the opposing portion to extend and contract about a straight line that connects a pair of side parts of the oral expiration guiding portion with each other.

4. The nasal adaptor according to claim 1, wherein the measurement member or the attaching portion includes a supporting portion that extends in the mouth-side guide path to be opposed to a rear surface of the opposing portion, wherein one of the rear surface of the opposing portion and the supporting portion includes a protruding part that protrudes toward another one of the rear surface of the opposing portion and the supporting portion, wherein the other one of the rear surface of the opposing portion and the supporting portion includes a receiving part that is recessed in correspondence to the protruding part, and wherein the positioning of the opposing portion is configured to be supported by the supporting portion by engaging the protruding part with the receiving part.

5. The nasal adaptor according to claim 4, wherein the other one of the rear surface of the opposing portion and the supporting portion includes a plurality of the receiving parts that are arranged in a vertical direction, and wherein the positioning of the opposing portion is configured to be changed stepwisely by engaging the protruding part with different one of the receiving parts.

6. The nasal adaptor according to claim 4, wherein the protruding part includes a concave part in which a part of an upper part is downwardly recessed, and wherein the receiving part includes a convex part that protrudes so as to be engaged with the concave part.

7. The nasal adaptor according to claim 1, wherein the measurement member is placed on a side of the attaching portion that is opposite to the living body, and attached to the attaching portion to cover at least a part of the attaching portion.

8. The nasal adaptor according to claim 1, wherein the measurement member is configured to have a rigidity that is higher than rigidities of the oral expiration guiding portion and the attaching portion.

9. The nasal adaptor according to claim 8, wherein the measurement member includes upper and lower fixing parts that are fixed to upper and lower parts of the attaching portion, respectively, so as to stretch the attaching portion in a vertical direction.

10. The nasal adaptor according to claim 8, wherein the measurement member includes right and left fixing parts that are fixed to right and left parts of the attaching portion, respectively, so as to stretch the attaching portion in a lateral direction.

11. The nasal adaptor according to claim 1, further comprising a nasal expiration guiding portion which is placed in correspondence with nostrils of the living body, which is integrally connected to an upper part of the attaching portion, and in which a nose-side guide path that guides expiration expired from the nostrils, toward the measurement member is formed.

12. A respiratory management device including:

the nasal adaptor according to claim 1; and a nasal cannula that has a tubular shape, and that is attached to the nasal adaptor in order to supply a predetermined gas to at least one of the nostrils of the living body and the mouth.

* * * * *